United States Patent [19]

Zichner et al.

[11] Patent Number: 4,662,889

[45] Date of Patent: May 5, 1987

[54] KNEE JOINT PROSTHESIS

[75] Inventors: Ludwig Zichner, Frankfurt; Erhard Dörre, Plochingen; Peter Prüssner, Dietzenbach; Horst von Borries, Krefeld, all of Fed. Rep. of Germany

[73] Assignee: Feldmühle Aktiengesellschaft, Düseldorf, Fed. Rep. of Germany

[21] Appl. No.: 603,659

[22] Filed: Apr. 26, 1984

[30] Foreign Application Priority Data

Apr. 28, 1983 [DE] Fed. Rep. of Germany ....... 3315401

[51] Int. Cl.⁴ ............................................. A61F 2/38
[52] U.S. Cl. ..................................................... 623/20
[58] Field of Search ....................... 623/16, 17, 18, 19, 623/20, 21, 22, 23; 128/92 C, 92 CA

[56] References Cited

U.S. PATENT DOCUMENTS

| 4,136,405 | 1/1979 | Pastrick et al. | 623/20 |
| 4,262,368 | 4/1981 | Lacey | 623/20 |
| 4,538,306 | 9/1985 | Dorre et al. | 623/18 |

Primary Examiner—Richard J. Apley
Assistant Examiner—David Isabella
Attorney, Agent, or Firm—Toren, McGeady and Goldberg

[57] ABSTRACT

A knee joint prosthesis includes a C-shaped femur cap to be fitted onto a resected femur condyle. The C-shaped femur cap is made up of two arch-shaped parts spaced apart and connected by a relatively flat third part. Each of the arch-shaped parts has a different radius. The arch-shaped part with the larger radius has an oblong hole extending in the circumferential direction of the part. A shaft can be placed through the oblong hole from the femur into the tibia. In addition, a tibia cap can be fitted onto the plateau of the tibia.

18 Claims, 9 Drawing Figures

KNEE JOINT PROSTHESIS

SUMMARY OF THE INVENTION

The present invention is directed to a knee joint prosthesis for the connection of the femur with the tibia and it includes a femur cap with a hook-shaped cross-section for partially enclosing the prepared femur condyles and simultaneous support on the tibia plateau along with a connecting member which can be implanted into the tibia.

Knee joint prostheses which replace the entire joint, require a resection of the entire joint and are known, for instance, from German Offenlegungsschrift No. 29 06 458 and German Offenlegungsschrift No. 25 49 819. In the design of a prosthesis, it is the goal to replace, if possible, only the sliding surfaces and still provide a firm guidance of the bony joint parts, even when there is ligament instability.

Therefore, it has been suggested in German Offenlegungsschrift No. 30 39 392 to resect the condylar area so that a femur cap can be attached with bone cement. Such a femur cap encloses the peripheral end of the resected femur and has as an outer surface two spherical areas which correspond to the condyles. These spherical areas are connected with a cup which replaces the tibia plateau and in which a pin attachment connects the two spherical segment-shaped areas. The cup is secured onto the tibia with bone cement. During hardening of the bond cement, however, a relatively high temperature develops so that temporary damage to the bone structure occurs. Further, antibody reactions and biomechanical factors, particularly in younger patients, argue against the use of bone cement. Accordingly, if possible, the use of bone cement should be avoided.

Therefore, it is the primary object of the present invention to provide an implantable joint which does not have the disadvantages experienced in the past and, while maintaining the physiological motion of the joint, that is the bending of the leg, even when the ligaments are damaged, assures a safe connection between the femur and tibia. In addition, the placement of the prosthesis should require as little bone resection as possible so that the option of a second operation is available. The so-called primary fixation is particularly important. In implants secured with bone cement, it is difficult to determine any difference between primary and secondary fixation, because the absolute anchoring effect takes place by means of the bone cement. As a result, the joint can be stressed after the hardening of the cement. If another type of attachment of the joint prosthesis is selected, such as screwing or nailing, the joint does not reach its full carrying capacity immediately. While it is fixed in the bone, that is the primary fixation, the final anchoring or securement takes place only as the bone grows in, and the prosthesis must first heal in place. The healing process takes longer when the primary fixation is weaker, because any movement between the bones and the implant disturbs the healing process. When the primary fixation is weak, the extremeties must be immobilized which is a considerable problem for the patient and there is also the danger of impairing the movement of the extremities when the healing period is overly long. Under such circumstances, thromboses and embolisms frequently occur.

Therefore, a preferred feature of the invention is to afford a knee joint prosthesis with very good primary fixation so that the healing process is shortened and an early stressing of the prosthesis can take place.

In accordance with the present invention, a knee joint prosthesis is connected to the femur and the tibia and includes a hook-shaped cross-section femur cap which partially encloses the resected femur condyles and is at the same time supported on the tibia plateau, and a connecting member implanted into the tibia and extending into the femur cap. The prosthesis is characterized by the following combination of features:

(a) the cross-section of the femur cap is C-shaped;

(b) the C-shaped cross-section of the femur cap is formed by two arches each having a different radius and connected to one another by a relatively flat surface member; and (c) in the portion of the femur cap having the larger radius arch, a hole, oblong in the circumferential direction, is arranged to receive a shaft which can be implanted into the tibia.

The C-shaped cross-section of the femur cap with its two arch-shaped parts permits a firm anchoring on the femur without using bone cement on the resected femur condyles. The primary fixation is achieved by the fit between the inner surface of the femur cap and the outer surface of the resected femur condyles. Due to the manner in which the cap is placed on the femur, a movement of the cap is possible in the direction of the axes of the arch-shaped parts. To prevent such movement, the femur cap is nailed or screwed to the femur or, according to a preferred embodiment of the invention, by engaging the shaft into a cylinder rotatably arranged within the femur cap in the region bounded by the larger radius arch-shaped part with the cylinder extending laterally beyond the opposite circumferential extending sides of the oblong hole. The cylinder is placed, practically without any play, between the two resected femur condyles and the cylinder has a bore arranged to receive the shaft. The shaft is anchored in the tibia. From the tibia, the shaft extends through the oblong hole in the region of the larger radius arch-shaped part of the femur cap for preventing any movement of the femur cap in the direction of the axis of the larger radius arch-shaped part.

Accordingly, a primary fixation of the femur cap is obtained in a practically ideal manner without the use of bone cement and this fixation has the further considerable advantage that the bone requires only minimum resecting.

The outer shape of the femur cap corresponds basically to the natural shape of the joint and is polished in accordance with an advantageous embodiment of the invention.

The tibia is supported twice. It is supported during compressive load on the outer periphery of the femur cap where an implant is used as replacement of the tibia plateau and, secondly, the tibia is connected by the shaft with the cylinder so that during the application of tensile stress, the sliding motion is displaced into the larger radius arch-shaped part of the femur cap, that is, between the surface of the cylinder and the inner surface of the femur cap. In an advantageous embodiment of the invention, the inner surface of the femur cap in the region of the larger radius arch-shaped part which adjoins the oblong hole, is polished.

To afford a further reduction in friction, the end faces of the cylinder which slide during movement of the knee on the resected sides of the femur condyles, can be polished. It is advantageous to polish the surface of the cylinder to assure that the friction between the cylinder and femur cap is maintained as low as possible.

Practically all biocompatible materials which have the necessary strength can be used for forming the prosthesis. Care must be taken, however, that the materials used do not cause abrasion when they move relative to one another. As an example, the femur cap can be formed of ceramic oxides or metal with the cylinder being made of HD-polyethylene. Combinations of ceramic oxides and metal or metal and metal cannot be used because there is the danger of metal abrasion due to movement. It is preferable if ceramic oxides are used for both the femur cap and the cylinder, because they have extremely low abrasion values which are practically zero and excellent compatability with the body. The term ceramic oxides is defined more precisely as sintered ceramic oxides of high purity, where the term "high purity" means that the sintered ceramic oxide has a purity exceeding 95%. Sintered metal oxides of zirconium, titanium and particularly aluminum, as well as mixtures thereof, are included under the term "sintered ceramic oxides" in view of the above explanation. It is preferable to use a sintered aluminum oxide having the following characteristics:

a density = or $> 3.92$ g/cm$^2$,
a porosity = or $< 2\%$,
a water absorption = or $< 0.01\%$,
a purity = or $> 99.7\%$ Al$_2$O$_3$,
a Vickers hardness (P = 2M) = or $> 22000$ N/mm$^2$,
an average grain size = or $< 10$ $\mu$m,
an average bending strength = or $> 320$ N/mm$^2$,
a compression strength = or $> 4000$ N/mm$^2$, and
a tensile strength = or $> 160$ N/mm$^2$.

Such a material affords the required high safety for a prosthesis over several decades, and due to the combination of the high density with the low average grain size and the high purity of the sintered aluminum oxide, excellent characteristics are attained. With regard to purity it is to be understood that in aluminum oxide there are as few foreign substances as additional components which could lead to a glassy intermediate or transition phase. It would not be contradictory of this requirement if the starting material, that is aluminum oxide, contained certain additives, for instance, magnesium oxide may be added as a grain growth inhibitor.

It is possible to polish a material so that it has very high values of smoothness and consequently extremely low friction is present as is necessary in a prosthesis, that is, the friction between the cylinder and the inner surface of the femur cap is very low as well as the friction between the end faces of the cylinder and the resected condyle surfaces contacted by the cylinder.

For the primary fixation of the femur cap, it is important that the measurements of the resected condyle surfaces exactly coincide with the inside measurements of the femur cap, so that the cap can be secured to the femur by a press fit. With a press fit connection, the use of bone cement is unnecessary. Further, with such a connection, an excellent primary fixation is achieved immediately. It is a prerequisite that the narrow tolerances are maintained during implantation and also during the manufacture of the femur cap. Therefore, the resection is carried out advantageously by means of a template-guided end milling cutter or plane milling cutter guided according to the inside shape of the femur cap. In an additional surgical step, the surfaces of the condyles are resected so that these spaced surfaces in the assembled joint form the contact with the end faces of the cylinder.

The cylinder is supported in the region of the larger radius arch-shaped part of the femur cap and this arch-shaped part extends through an angle $\alpha$ in the range of 130° to 190°. Accordingly, this arch-shaped part provides a good support for the cylinder within the femur cap and also makes it possible to provide a solid attachment of the femur cap to the femur.

The angular extent of the smaller radius arch-shaped part, in accordance with the present invention, is in the range of 120° to 160° so that in the normal case it encloses only a small partial area of the facies patellaris, if a larger resection of the femur part was necessary, the arch-shaped part can be extended higher for completely replacing the facies patellaris and, if necessary, also the patella.

In a preferred embodiment of the present invention, the inner radius of the larger radius arch-shaped part is in the range of 8 to 25 mm, the inside radius of the smaller radius arch-shaped part is in the range of 4 to 15 mm and the surface extending between the two arch-shaped parts has a relatively flat configuration with a radius in the range of 20 to 150 mm. The selection of the radii depends on the condition of the bone structure, that is, the size of the joint to be replaced and the amount of the bone substance to be resected, and it also depends on the material used for the femur cap. The basic prerequisite is that the least amount of bone structure is to be removed as can be justified. This requirement provides the opportunity to afford the possibility of a second operation at a point in time significantly later and also that, in the event the implantation of the prosthesis is no longer possible, a joint stiffening can be undertaken without any considerable shortening of the leg. Shortening results primarily from the thickness of the implant materials used and, according to a preferred embodiment of the invention, the thickness of the femur cap should not be less than 4 mm and not exceed 20 mm. The lower limit of 4 mm permits the safe use of a metal implant though in a femur cap formed of ceramic oxide the thickness would be greater, preferably not less than 6 mm. As already mentioned, the upper limit of 20 mm is the result of a shortening which occurs during stiffening of the joint by a second operation which also should be as minor as possible.

When using ceramic oxides which are preferred because of their greater hardness and thus low susceptibility to wear, it is possible to select the radii so that they are not too small because the processing step, such as grinding and polishing can be better controlled. Furthermore, during the pressing of the ceramic oxide powder in a mold, a more uniform material flow, and as a result, a more uniform distribution of strength results. It is preferable to maintain the radius above its lower limit, that is, for the inside radius of the smaller radius arch-shaped part of 4 mm.

The oblong hole formed in the femur cap extends in an angular range of 90° to 140°, accordingly, the shaft guided in the oblong hole can be moved through an angle of at least 90° up to a maximum of 140°, in other words, the full motion of the knee joint is possible.

In a preferred embodiment of the invention, in the region of the oblong hole, the shaft is provided with a guide sleeve. The guide sleeve is made of the same ceramics material as the femur cap and surrounds the metallic shaft in the region of the oblong hole so that during movement of the joint, that is, during bending of the knee, the ceramic oxide material slides on ceramic oxide material and no metal abrasion can take place.

If the femur cap is a metal implant then, to prevent metallic abrasion, the sliding cylinder within the cap is formed of HD-polyethylene, that is, a plastics material. In such an arrangement, the guide sleeve would not be made of a ceramic oxide, because it would lead to metallic abrasion in the region of the oblong hole in the femur cap. Accordingly, the guide sleeve is preferably made of the same plastics material as the cylinder.

The shaft is formed of a material usually employed for metal implants, such as an alloy containing chromium, nickel, molybdenum and cobalt or titanium. If the cylinder into which the shaft is to be attached is formed of high pressure polyethylene, the shaft may be connected with the cylinder by means of a snap-in connection. In such a connection, the shaft is provided in the engagement region within the cylinder with an annular groove and the cylinder has an annular protuberance corresponding to the groove. The shaft can be attached within the cylinder by pressing it into the bore formed in the cylinder so that the annular protuberance seats within the annular groove.

In another preferred arrangement of the invention the cylinder has a frusto-conical bore and the shaft is provided with a frusto-conical section for engagement within the bore. In this arrangement, the cylinder containing the frusto-conical bore is formed of a sintered ceramic oxide material and the shaft with a corresponding frusto-conical section has a deformable surface. Due to the interaction of the two frusto-conical surfaces, an automatic locking effect is achieved so that the shaft is firmly secured within the cylinder.

The invention also includes a tibia cap arranged to be used with the femur cap. Direct action of the femur cap on the cartilage of the tibia plateau leads to a punctiform and linear stress on the cartilage and consequently to its regression. This occurs because the outer shape of the femur cap is selected to correspond to the shape of the natural bone structure, however, it is not possible to achieve a complete adaptation, since the dimensions of the condyles change and as a result the tibia plateau, in engagement with the condyles, is differently formed. The punctiform and/or linear stress caused by the femur cap and causing the regression of the cartilage, then acts directly on the tibia plateau whereby bone regression takes place, accordingly, the coordination of the tibia cap to the femur cap is particularly important.

The tibia cap in this embodiment of the invention has a C-shaped cross-section and is provided in the region of the eminentia intercondylaris with a bore to receive the shaft. A plastics material, preferably HD-polyethylene, is the preferred material for the interaction with the femur cap whether it is formed of metal or of ceramic oxide. In either case, the damping action during sudden movement is very advantageous, however, it is also important that in the combination of a ceramic oxide femur cap with a HD-polyethylene tibia cap that excellent low friction values are achieved. The outer configuration of the tibia cap is selected based on the natural shape of the tibia plateau, that is, it has at both sides of the eminentia intercondylaris one cap to hold the femur condyles. Due to its C-shaped cross-section, the tibia cap can be pushed onto the tibia after the completed resection of the tibia plateau, so that the securement of the tibia cap is effected without the use of bone cement. The primary fixation can also be effected by means of screws or nails. It is more advantageous, however, to insert the shaft into the tibia through a bore in the tibia cap in the region of the eminentia intercondylaris.

In any case, it is necessary to place the shaft in the tibia when a femur cap is to be implanted. If a tibia cap is also to be implanted, then the same shaft can be used to fix both the femur cap and the tibia cap in position and such an arrangement represents a considerable improvement over the art.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE INVENTION

Figure 1:
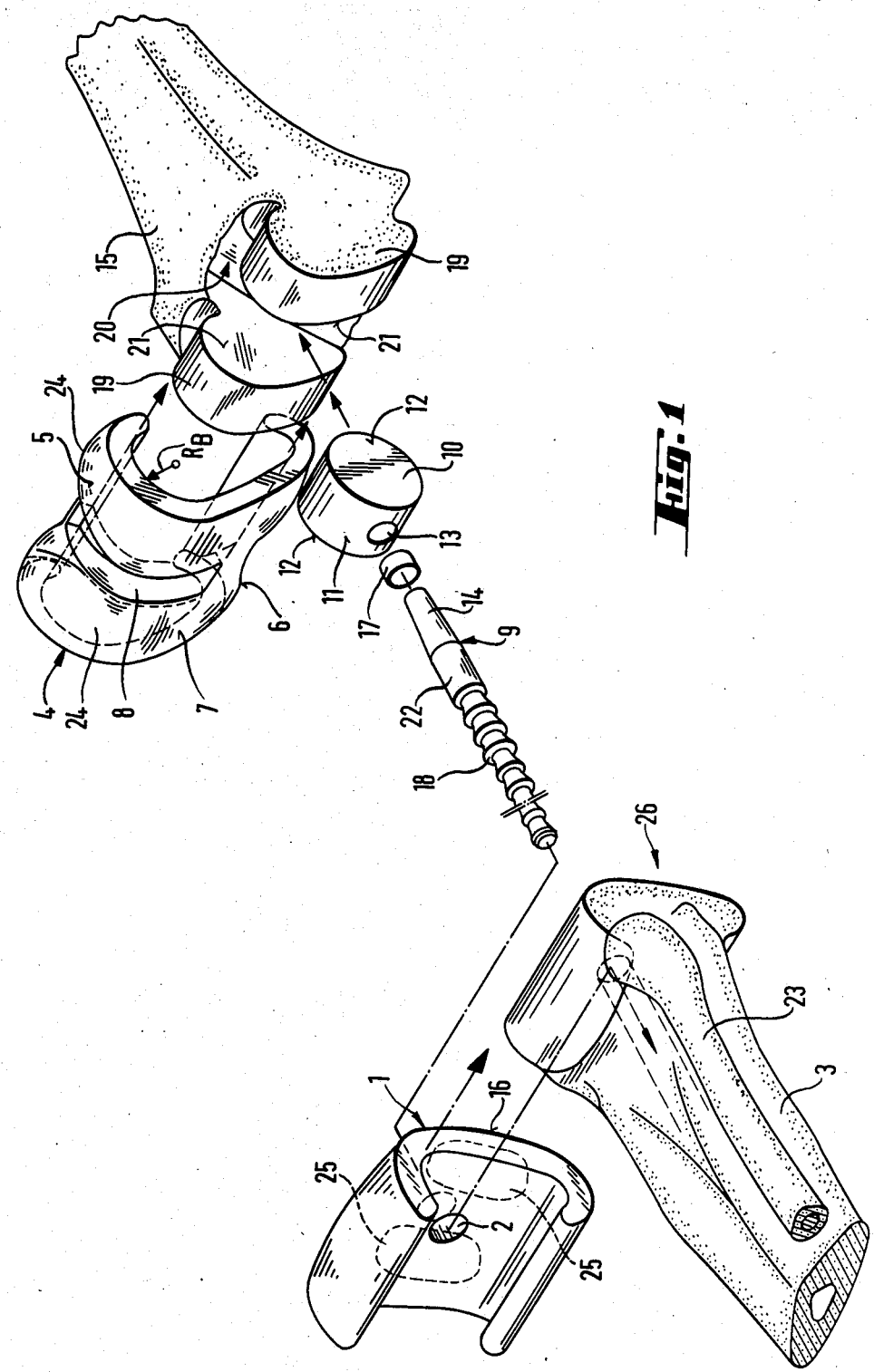
FIG. 1 is an exploded perspective view of a prosthesis embodying the present invention.

In FIG. 1, femur 15 is resected in the region of the condyles 19 in the circumferential direction so that a femur cap 4 can be slid onto the end of the femur. Perpendicularly to the circumferentially extending surfaces, the condyles 19 are resected on the adjacent sides so that generally parallel surfaces 21 are formed in the region of the fossa intercondylaris 20. During the assembly of the prosthesis, a cylinder 10 is placed between the surfaces 21 so that its end faces 12, extending transversely of the circumferentially extending cylindrical surface 11, contact the surfaces 21 of the condyles. In the assembled position, the cylinder 10 has a frusto-conical bore 13 directed toward the tibia 3. Further, the cylindrical surface 11 of the cylinder 10 bears against the fossa intercondylaris 20.

Figure 2:
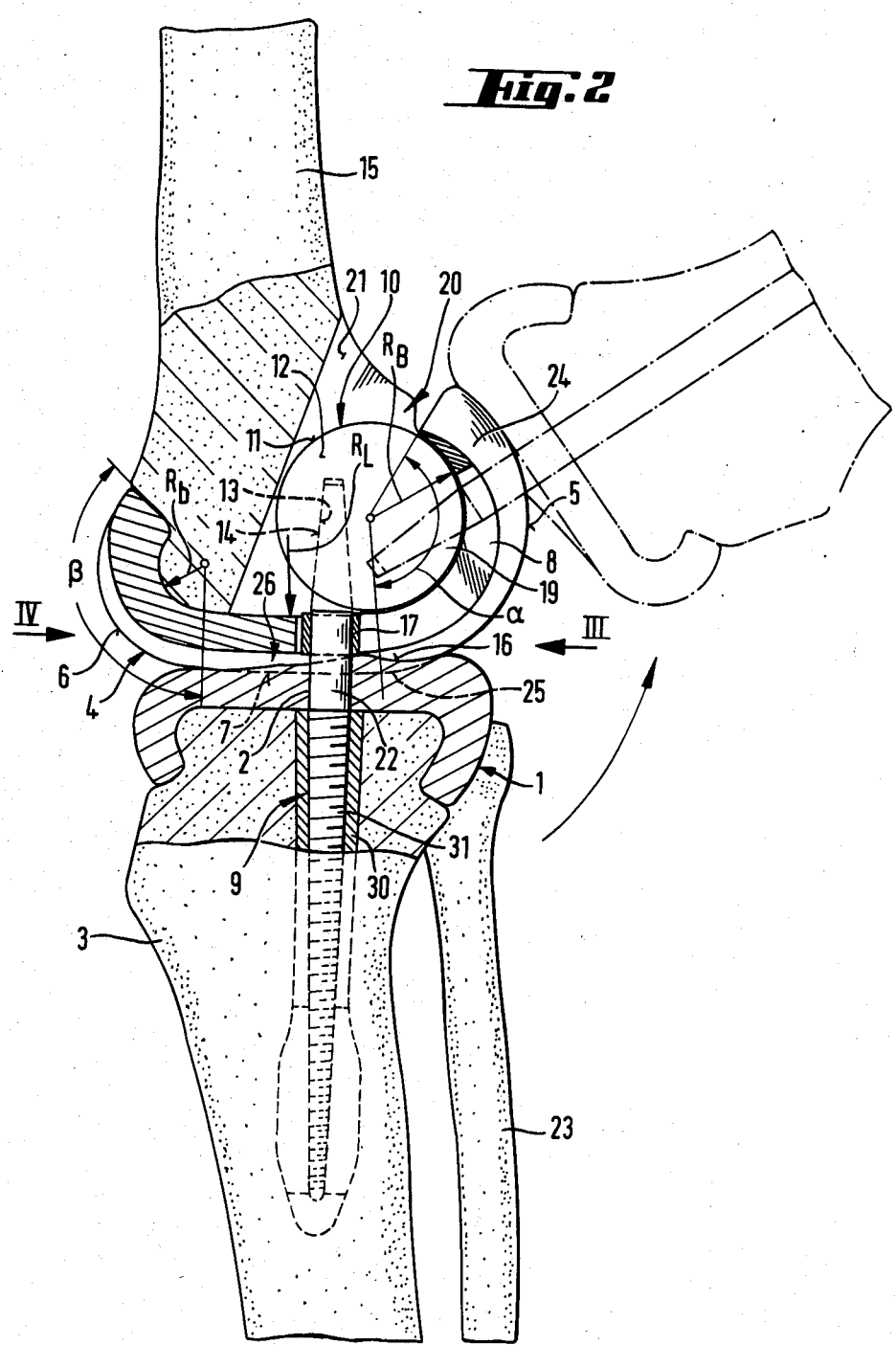
FIG. 2 is a side view, partly in section, of another implanted prosthesis.

As can be seen in FIG. 1 and FIG. 2 the femur cap 4 is formed by two oppositely arranged arch-shaped parts 5, 6, the arch-shaped part 5 has a larger radius than the arch-shaped part 6. A relatively flat surface part 7 extends between the two arch-shaped parts 5, 6. The inside radius $R_B$ of the arch-shaped part 5 is in the range of 8 to 25 mm, while the inside radius $R_b$ of the arch-shaped part 6 is in the range of 4 to 15 mm. The part 7 extending between the two arch-shaped parts 5, 6 has a slight curvature as compared to these arch-shaped parts with inside radius $R_L$ in the range of 20 to 150 mm.

Further, as is also shown in FIG. 2, the larger radius arch-shaped part 5 has an angular range α in the range of 130° to 190° while the smaller radius arch-shaped part 6 has an angular range β in the range of 120° to 160°.

The arch-shaped part 5 is provided with an oblong hole 8 extending in the circumferential or curved direction of the arch-shaped part. The oblong hole has an angular extent in the range of 90° to 140°.

By pressing the C-shaped femur cap 4 onto the resected condyles 19, note the direction of the arrows showing the movement of the cap in FIG. 1, and with the cylinder 10 fitted into the space between the surfaces 21 on the condyles 19, the cylinder 10 is located within the arch-shaped part 5 of the femur cap and the oblong hole 8 affords access to the frusto-conical bore 13, note FIG. 2, within the cylinder 10. Note that the bore 13 is located eccentric to the center of the cylinder 10 and extends chordally of the cylinder. In the assembled position, the cylindrical surface 11 of the cylinder 10 rests against the fossa intercondylares 20.

As can be seen in FIG. 1, the plateau of the tibia 3 is resected to receive the tibia cap 1. As can be seen in FIGS. 1 and 2, the tibia cap 1 has a pair of opposite arch-shaped parts each with a different radius similar to the arrangement of the femur cap 4. Tibia cap 1 is provided with a bore 2 in the region of the eminentia intercondylaris 16. After fitting the tibia cap 1 on the tibia 3, a bore is formed in the tibia 3 for receiving the shaft 9. The shaft 9 is driven through the bore 2 into the bore formed in the tibia 3. As indicated in FIG. 1, the portion of the shaft 9 to be inserted into the bore in the tibia is provided with outwardly projecting support ribs 18 so that a secure attachment is effected in the tibia 3. At the end of the support ribs 18 closer to the femur 15, the shaft has a cylindrical area 22 which serves to hold a guide sleeve 17. Extending from the cylindrical section 22 as viewed in FIG. 1 toward the femur there is a frusto-conical section 14 which has a taper angle in the range of 1:10 to 1:20 and it engages into the frusto-conical bore 13 in the cylinder 10. The tibia cap 1 is designed so that the fibula 23 usually does not have to be resected.

Figure 3:
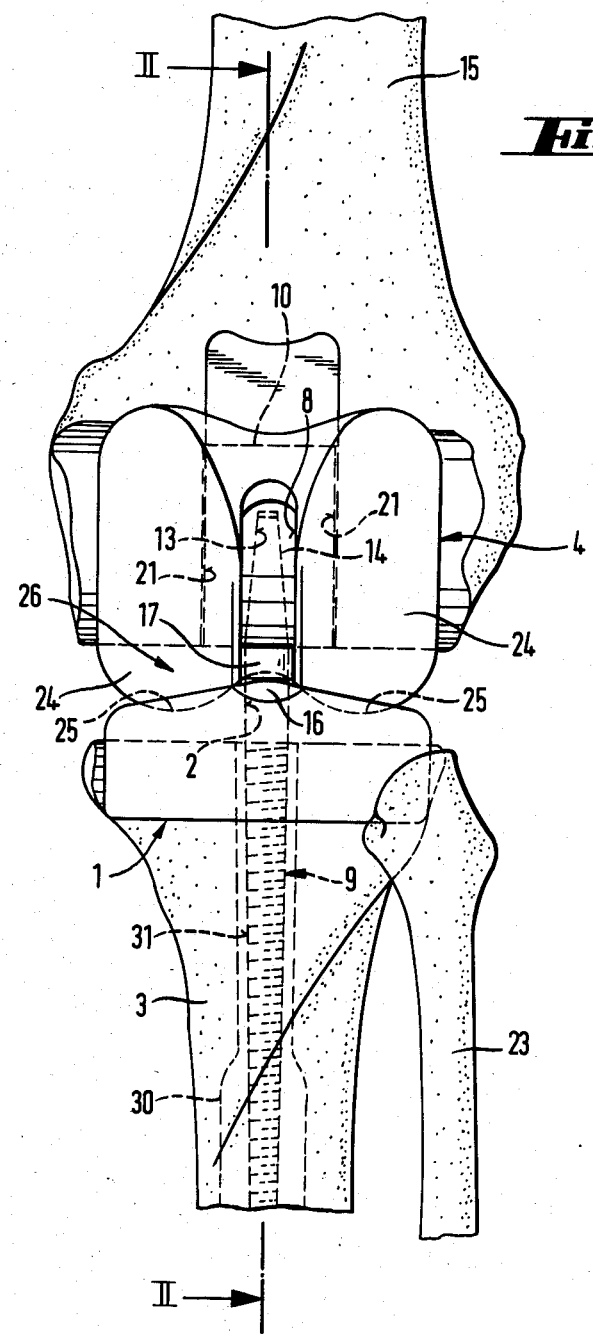
FIG. 3 is a rear view of the implanted prosthesis in FIG. 2.
Figure 4:
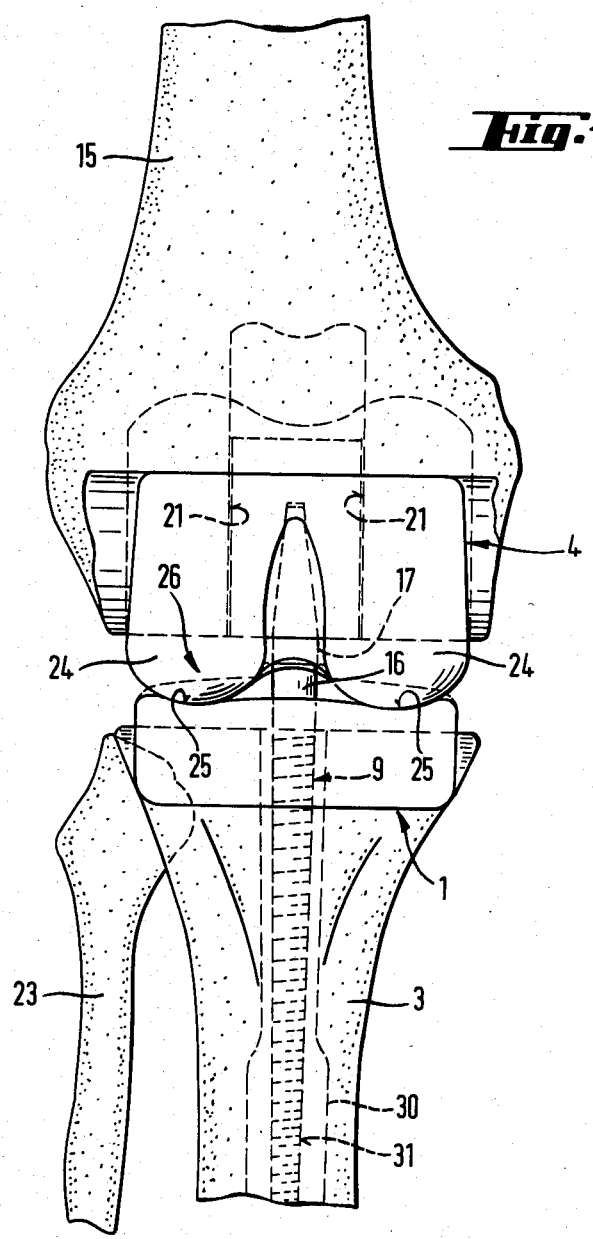
FIG. 4 is a front view of the implanted prosthesis in FIG. 2.
Figure 8:
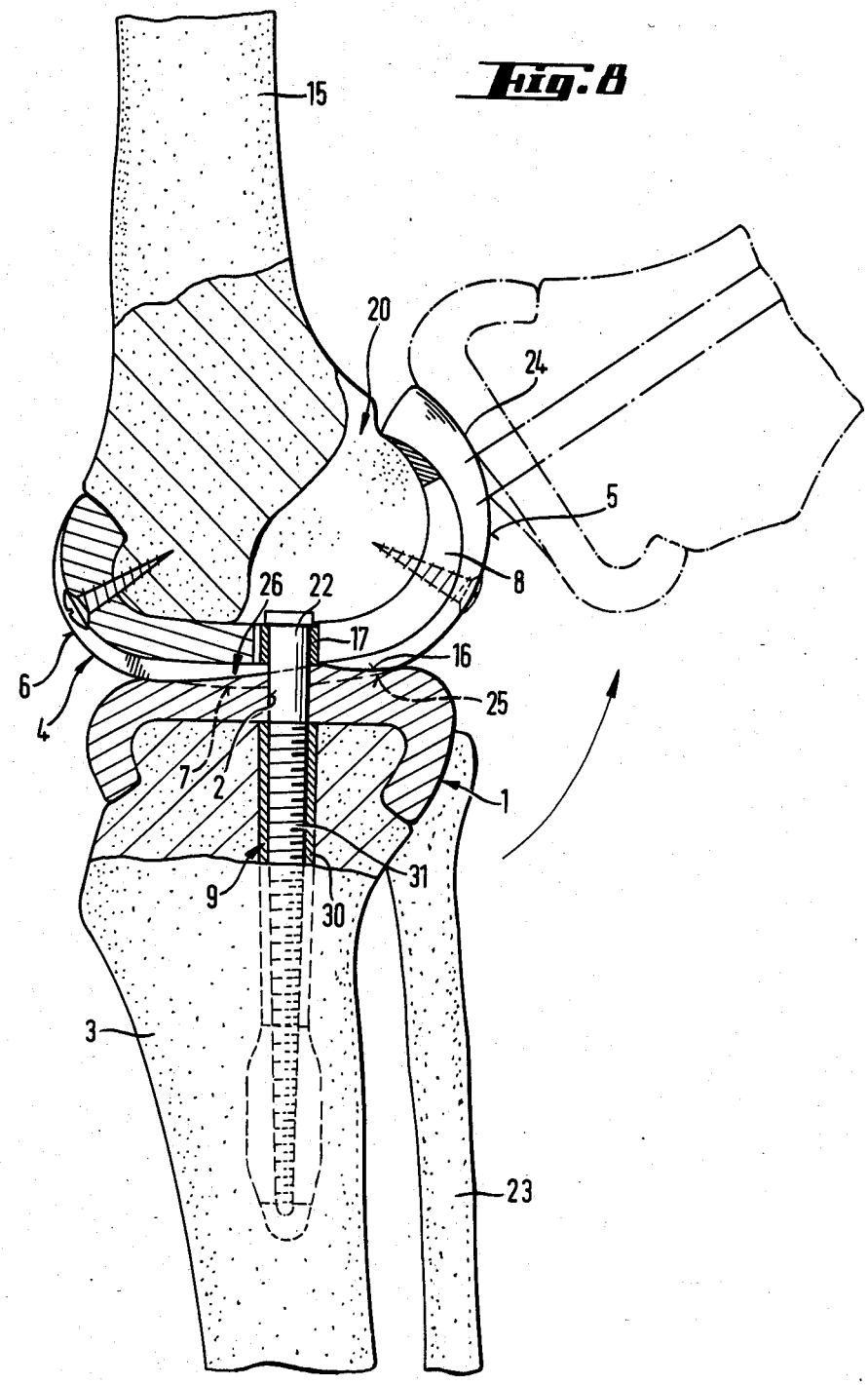
FIG. 8 is another arrangement of the embodiment shown in FIG. 5 in which a cylinder is not inserted into the condyle region of the femur.

In FIGS. 2, 3 and 4 and also in FIG. 8 another embodiment of the shaft is illustrated. In these figures, the shaft 9 is provided with a threaded insert 31 which is placed within an expansion dowel sleeve 30. By rotating the threaded insert 31, the expansion dowel sleeve 30 is pressed against the wall in the bore of the tibia 3 and fixes the tibia cap in position on the end of the tibia 3.

Figure 5:
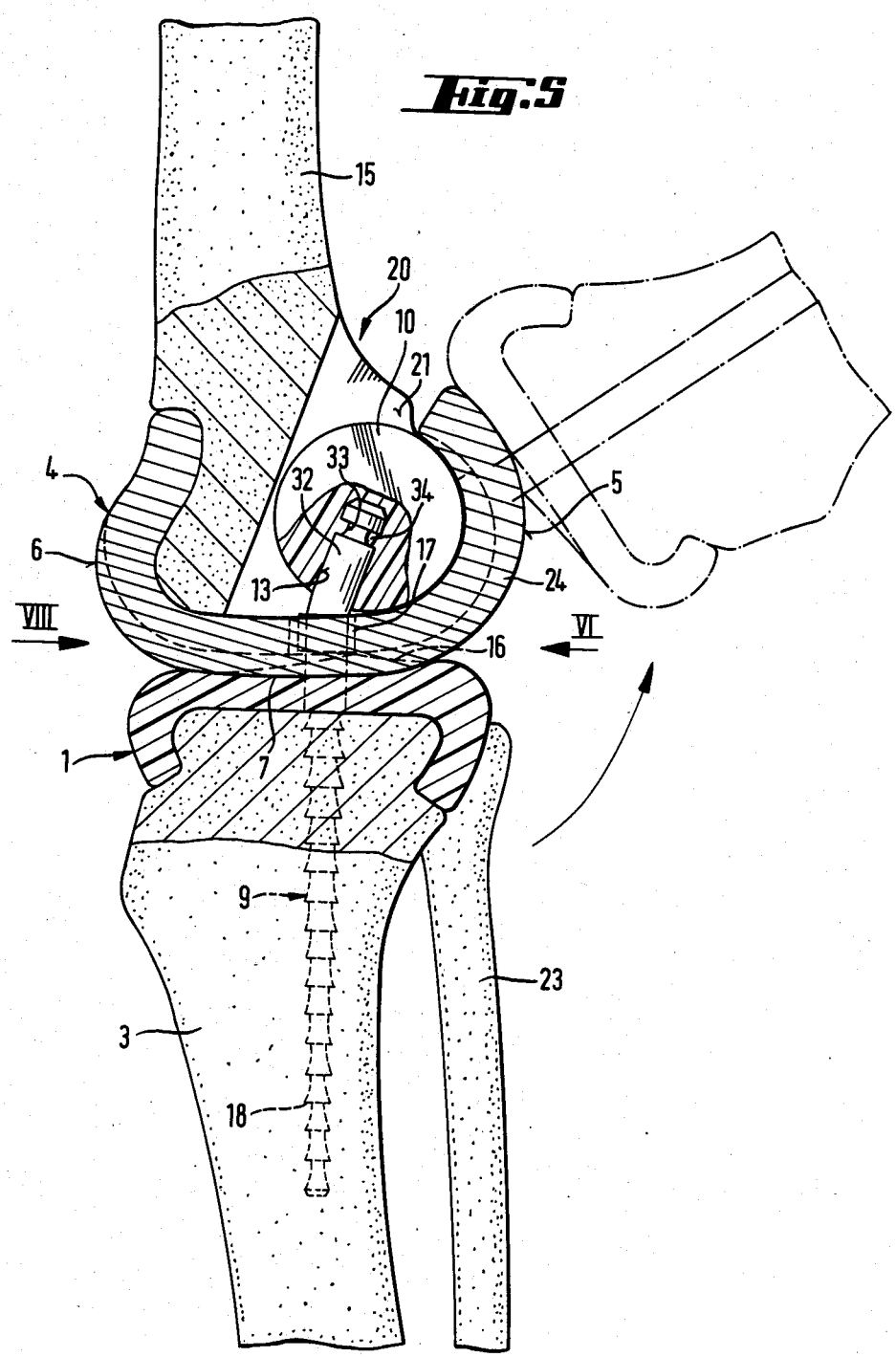
FIG. 5 is a side view partially in section of the prosthesis embodying the present invention showing another embodiment of the shaft.
Figure 6:
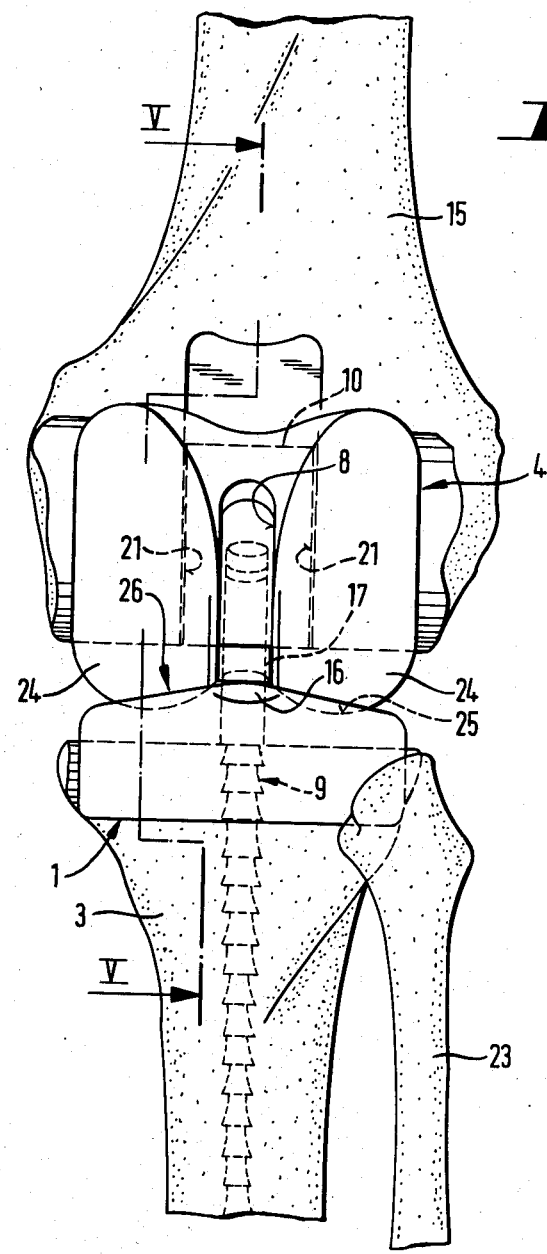
FIG. 6 is a rear view of the prosthesis shown in FIG. 5.
Figure 7:
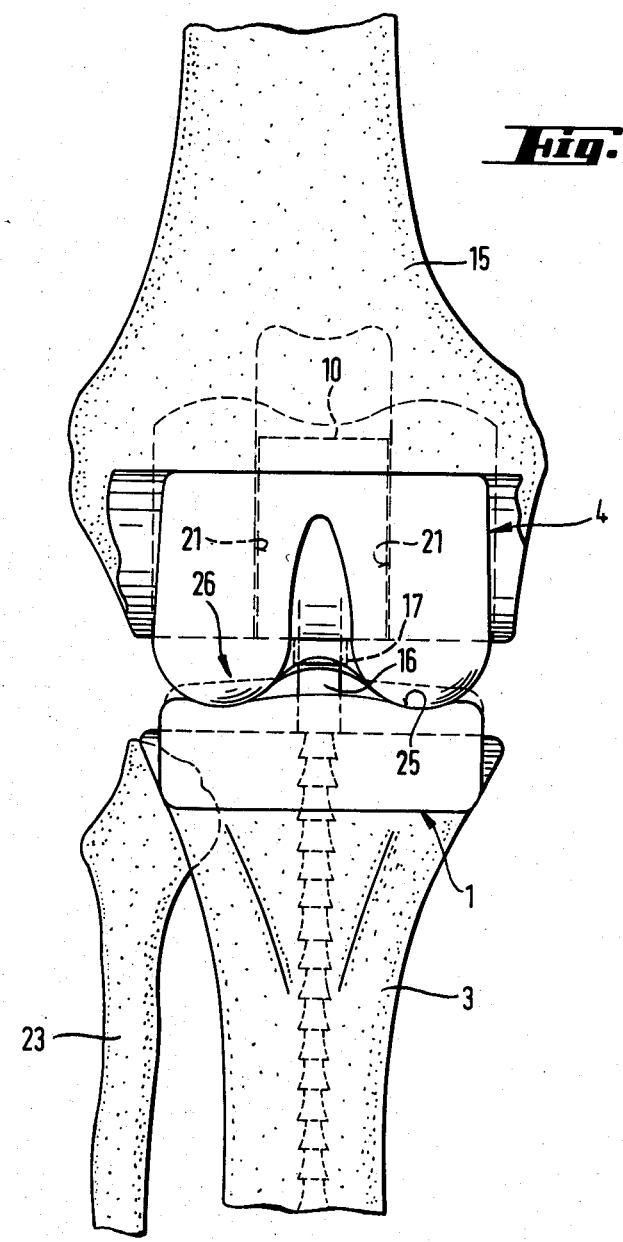
FIG. 7 is a front view of the prosthesis shown in FIG. 5.

In FIG. 5, a variation of the shaft 9 shown in FIG. 1 is provided with the end of the shaft inserted into the cylinder 10 being bent angularly relative to the remainder of the shaft extending through the femur cap 4 and the tibia cap 1 into the tibia 3. The bent section of the shaft 9 within the cylinder 10 is in the form of a cylindrical pin 32. Adjacent the end of the shaft 9, the cylindrical pin 32 has an annular groove 33 extending around the pin and an annular protuberance 34 formed by the material of the cylinder and extending into the bore in the cylinder engages within the annular groove. In this embodiment, the cylinder is formed of HD-polyethylene and the end of the cylinder pin 32, first inserted into the bore 13 in the cylinder, is frusto-conically chamfered so that it can be inserted into the bore 13. As the pin is driven into the bore 13, it presses the annular protuberance 34 outwardly due to the elasticity of the material forming the cylinder until the end of the pin reaches the inner end of the bore and the annular protuberance 34 rebounds inwardly and engages within the annular groove 33. As a result, the shaft 9 is firmly anchored within the cylinder 10.

As viewed in FIG. 5, with the leg in the straightened or extended position, the part 7 of the femur cap 4 is located practically horizontally, that is, perpendicular to the axis of the femur 15. The condyle reconstruction part 24 of the femur cap 5, that is, the outside surface of the arch-shaped part 5 is approximately barrel-shaped and rests in the complementary shaped cups 25 of the tibia cap, note FIGS. 2 to 4.

In FIGS. 2 to 8 an implanted femur cap 8 is shown in direct engagement with the tibia cap 1. In the embodiments illustrated in FIGS. 2 to 7, similar to that displayed in FIG. 1, the engagement of the shaft 9 in the cylinder 10 is shown and while it is extremely advantageous, it is not required in each operation. FIG. 8 displays the femur cap 4 fixed in place by a screw attachment so that it is not necessary to resection the region of the fossa intercondylaris 20. In this embodiment, however, the shaft is still required for guidance, however, it is of a shorter construction, that is, it only projects through the oblong hole 8 of the femur cap. It does not project to any significant amount into the region of the fossa intercondylaris 20. Further, the shaft 9 extends through a guide sleeve 17 held on the shaft by means of the head 35 on the end of the shaft 9 projecting through the oblong hole 8.

In FIG. 5 the smaller radius arch-shaped part 6 of the femur cap 4 extends upwardly further into the femur 15 and this arrangement is required when the patella must be replaced. This extended portion of the arch-shaped part 6 serves as a guide for the artificial patella.

Figure 9:
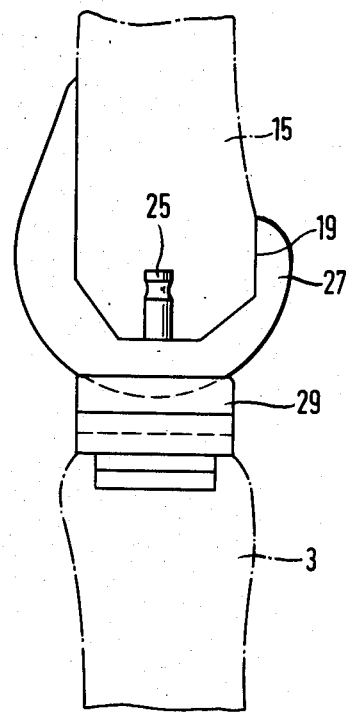
FIG. 9 is a side view of a prosthesis exemplary of the state of the art.

In FIG. 9 the state of the art is displayed with the femur 15 being resected to a greater degree in the region of the condyles 19 and this region is surrounded by a hook-shaped implant 27. The hook-shaped implant 27 is secured by cement and a holding pin 25. Further, the implant 27 rests on a support plate 29 secured by cement into the tibia 3.

Various surfaces of the prosthesis are polished to limit friction during use of the prosthesis. For example, the inside surface of the femur cap in the region of the oblong hole 8, located in the larger radius arch-shaped part 5, is polished. Further, the outer surface of the femur cap is also polished. When the embodiment as illustrated in FIG. 1 is used, both the cylindrical surface 11 and the end faces 12 of the cylinder are polished.

While specific embodiments of the invention have been shown and described in detail to illustrate the application of the inventive principles, it will be understood that the invention may be embodied otherwise without departing from such principles.

We claim:

1. An implantable knee joint for connecting the femur with the tibia comprising a femoral cap having a C-shaped cross-section for partial enclosure of the resected femoral condyles and for abutment and support on the tibial plateau, said cap having an inner and outer surface; said outer surface shaped to serve as a sliding surface for a corresponding tibial member and said inner surface being mechanically connectable to said resected condyles, wherein the improvement comprises said cap having two arcuate shaped bearing surfaces separated by an oblong cut-out extending in a circumferential direction about said cap wherein said cut-out is in substantially coincidence with a similar shaped slot formed in said resected condyles; and an axially extending cylindrically substantially disc-shaped sliding member disposed in said slot to directly abut the bony tissues of said resected condyles and said disc-shaped sliding member being coupled to a connecting member, said connecting member being an elongated shaft having a first and second ends wherein said first end is arranged to extend into and mechanically anchor within the tibia and the second end extending out of said tibia through said cut-out into a closely fitted engagement with said disc-shaped sliding member thereby actively connecting the femur with the tibia.

2. An implantable knee joint, as set forth in claim 1, wherein said disc-shaped sliding member comprises a cylindrical surface and a pair of spaced end surfaces extending transversely of the cylindrical surface and arranged to abut the bony tissues of said resected condyles, said cylindrical surface being located adjacent the inner surface of said cap with said cylindrical surface extending laterally outwardly from said oblong cut-out on both sides thereof extending in the oblong direction.

3. An implantable knee joint, as set forth in claim 1 or 2, wherein the inner surface of said cap extending along and adjoining said cut-out in the oblong direction thereof. is polished.

4. An implantable knee joint, as set forth in claim 1 or 2, wherein the outer surface of said femoral cap is polished.

5. An implantable knee joint, as set forth in claim 1 or 2, wherein said bearing surfaces each have a first end part and a second end part extending in and spaced apart in the circumferential direction by a third part and said first end part extends circumferentially for an angular extend in the range of 130° to 190°.

6. An implantable knee joint, as set forth in claim 1 or 2, wherein said bearing surfaces each have a first end part and a second end part extending in and spaced apart in the circumferential direction by a third part and said second end part extends angularly in the circumferential direction in the range of 120° to 160°.

7. An implantable knee joint, as set forth in claim 1 or 2, wherein said bearing surfaces each have a first end part and a second end part extending in and spaced apart in the circumferential direction by a third part and said third part in the direction extending between said first and second end parts has an inside radius in the range of 20 to 150 mm.

8. An implantable knee joint, as set forth in claim 1 or 2, wherein the wall thickness of said femoral cap is in the range of 4 to 20 mm.

9. An implantable knee joint, as set forth in claim 5, wherein the inside radius of said first end part is in the range of 8 to 25 mm.

10. An implantable knee joint, as set forth in claim 6, wherein the inside radius of said second end part is in the range 4 to 15 mm.

11. An implantable knee joint, as set forth in claim 5, wherein said oblong cut-out extends angularly in the circumferential direction of said first end part in the range of 90° to 140°.

12. An implantable knee joint, as set forth in claim 1 or 2, wherein a guide sleeve is located around said connecting member in the region where said connecting member extends through said oblong cut-out.

13. An implantable knee joint, as set forth in claim 2, wherein said cylindrical surface of said disc-shaped sliding member is polished.

14. An implantable knee joint, as set forth in claim 13, wherein said end faces of said disc-shaped sliding member are polished.

15. An implantable knee joint, as set forth in claim 12, wherein said disc-shaped sliding has a frusto-conical bore located therein extending inwardly from said cylindrical surface and said connecting member has a complementary frusto-conical surface thereon arranged to engage in said frusto-conical bore in said disc-shaped sliding member.

16. An implantable knee joint, as set forth in claim 1 or 2, wherein said tibial member comprises a tibial cap arranged to cooperate operatively with said femoral cap.

17. An implantable knee joint, as set forth in claim 16, wherein said tibial cap is C-shaped in cross-section.

18. An implantable knee joint, as set forth in claim 16, wherein said tibial cap has a region thereon corresponding to the eminentia intercondylaris, and said tibial cap has a bore extending through the region corresponding to the eminential intercondylaris for receiving said connecting member.

* * * * *